United States Patent [19]

Loponen

[11] Patent Number: 5,486,818
[45] Date of Patent: Jan. 23, 1996

[54] WIRELESS SWITCH FOR A TELEMETRIC RECEIVER

[75] Inventor: Erkki Loponen, Mikkola, Finland

[73] Assignee: Polar Electro Oy, Kempele, Finland

[21] Appl. No.: 340,479

[22] Filed: Nov. 14, 1994

Related U.S. Application Data

[63] Continuation of Ser. No. 918,052, Jul. 24, 1992, abandoned.

[30] Foreign Application Priority Data

Jul. 26, 1991 [FI] Finland .................................. 913599

[51] Int. Cl.⁶ .................................................. G08C 19/06
[52] U.S. Cl. .................... 340/870.31; 128/696; 128/903; 607/32; 607/60
[58] Field of Search .......................... 340/870.31; 379/38; 128/903, 687, 696; 607/32, 60, 30

[56] References Cited

U.S. PATENT DOCUMENTS

| | | | |
|---|---|---|---|
| 3,603,946 | 9/1971 | Lee | 128/903 |
| 4,528,987 | 7/1985 | Slocum | 128/903 |
| 4,541,431 | 9/1985 | Ibrahim et al. | 128/903 |
| 4,550,731 | 11/1985 | Batina et al. | 128/903 |
| 4,625,733 | 12/1986 | Saynajakangas | 128/903 |
| 4,700,707 | 10/1987 | Batina et al. | 607/32 |
| 4,979,506 | 12/1990 | Silvian | 128/903 |

FOREIGN PATENT DOCUMENTS 68734   10/1985   Finland .

*Primary Examiner*—John K. Peng
*Assistant Examiner*—Daniel J. Wu
*Attorney, Agent, or Firm*—Finnegan, Henderson, Farabow, Garrett and Dunner

[57] ABSTRACT

The invention relates to a wireless switch for a telemetric receiver in a pulse meter, comprising a switch (7) for detecting the intensity of a telemetric signal received in the telemetric receiver and actuating the desired function of the pulse meter when the signal exceeds a predetermined threshold value. In the invention, the inductance (L1) by which the receiver establishes an inductive coupling with a transmitter in telemetric pulse measuring is used as a detector in the switch (7) for detecting the intensity of the telemetric signal.

10 Claims, 2 Drawing Sheets

WIRELESS SWITCH FOR A TELEMETRIC RECEIVER

This application is a continuation, of application Ser. No. 07/918,052, filed Jul. 24, 1992, now abandoned.

BACKGROUND OF THE INVENTION

The present invention relates to a wireless switch for a telemetric receiver.

Telemetric data transmission is well-known, see e.g. FI Patent 68734, which discloses a telemetric measuring device for measuring pulse and ECG signals. Such a telemetric transmitter mainly comprises transmitter electronics enclosed in a casing and secured e.g. by two press studs to a belt keeping the transmitter in position, and electrodes connected electrically to the transmitter electronics and attached to the belt on the side facing the user's skin on both sides of the transmitter electronics (two electrodes).

Receivers known from the prior art usually comprise not only a pulse measuring function but also clock and timing functions and various programming possibilities for alarm signalling and the like. Therefore it has been necessary to provide the casing, which is as small as possible (equal in size to a wrist watch), with several press buttons so as to be able to use all the features of the measuring device. One press button is usually reserved solely for the actuation of the basic function, that is, the pulse measuring, the device being switchable e.g. between the clock mode and the pulse measuring mode by pressing the button. It is obvious that it should be possible to activate and terminate the pulse measuring function as easily as possible by a single press button, and so very many other functions cannot be arranged to be actuated by this button.

The provision of a great number of press buttons in a casing equal in size to a wrist watch is difficult as well as contradictory to an attempt to minimize the size of the casing, which as such is possible from the electronic point of view. For the ease of use, the size of the press buttons cannot be reduced without limits nor can they be embedded in the structure so that they could not be pressed by finger tips alone. The device is an accessory means for e.g. a sportsman, and so it should be as simple and rapid to use as possible.

SUMMARY OF INVENTION

The object of the present invention is to provide a wireless switch for a telemetric receiver unit which avoids the above-mentioned disadvantages. To achieve this, the switch according to the invention comprises a means for detecting the intensity of a telemetric signal received in the telemetric receiver and actuating a desired function of the pulse meter when the signal exceeds a predetermined threshold value, wherein the inductance, by means of which the receiver of the pulse meter establishes an inductive coupling with a transmitter in telemetric pulse measuring, is used as a detector in the means for detecting the intensity of the telemetric signal.

According to the invention, the press buttons for e.g. switching the device on and off need not be provided in the casing of the receiver. So one advantage of the invention is that the starting takes place nearly automatically, instinctively, which is of advantage especially in intra-performance start-ups where the sportsman has to fix his eyes and center his attention strictly to the course of the game or performance. Another advantage is that other desired functions may be actuated when the pulse measuring function has already been switched on.

The other preferred embodiments of the invention are characterized by what is disclosed in the enclosed claims.

BRIEF DESCRIPTION OF DRAWINGS

In the following the invention will be described in greater detail by way of example with reference to the attached drawings, in which.

DESCRIPTION OF PREFERRED EMBODIMENT

Figure 1:
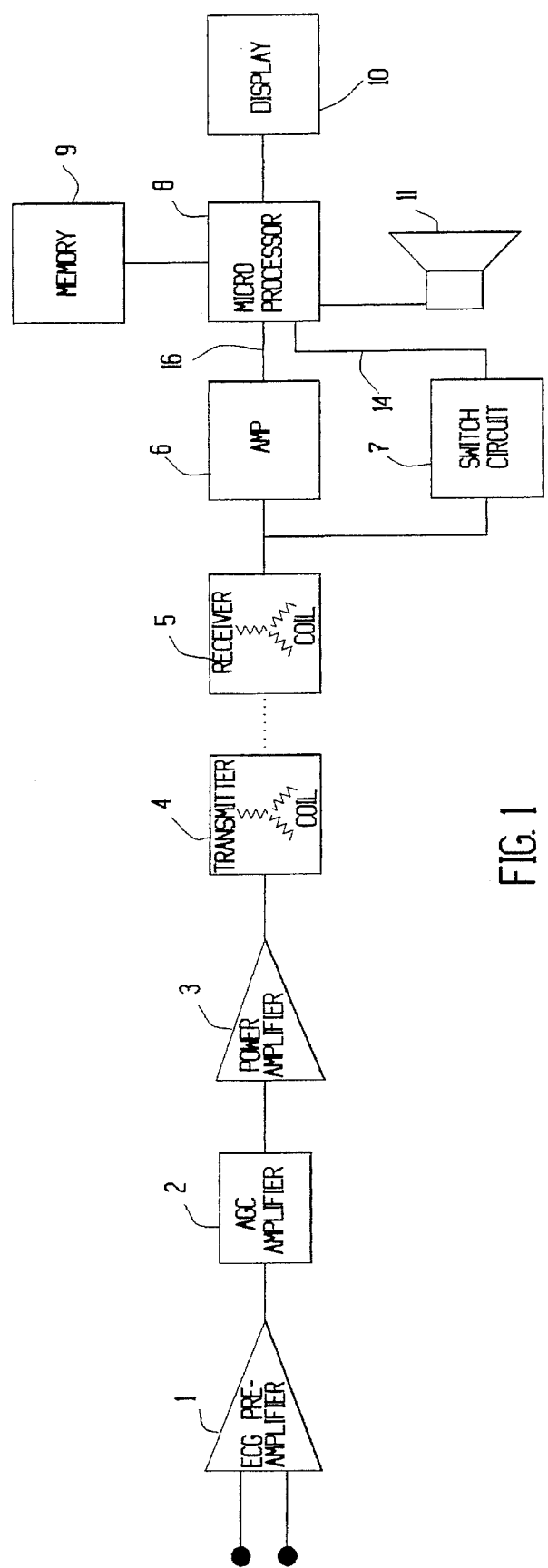
FIG. 1 shows a block diagram illustrating the main components of a telemetric receiver and transmitter.

FIG. 1 shows an ECG preamplifier 1 provided in a transmitter, electrodes (not shown) sensing the pulsation of the heart being connected to the preamplifier. The signal of the preamplifier 1 is amplified in an AGC amplifier 2 and further in a power amplifier 3. The amplified signal is applied to a transmitter coil 4 creating a magnetic field which is detected by a receiver coil 5. The received signal is amplified similarly as in the transmitter by means of an amplifier circuit 6. The amplified signal is applied to a microprocessor 8, to which a memory 9 and a display device 10 are connected, as described in U.S. Pat. No. 9,625,733 referred to above. The receiver usually also comprises a small loudspeaker 11 for forwarding pace or alarm signals to the user. The structure and operation of a wireless switch circuit 7, which is an essential part of the invention, will be described more closely below.

Figure 2:
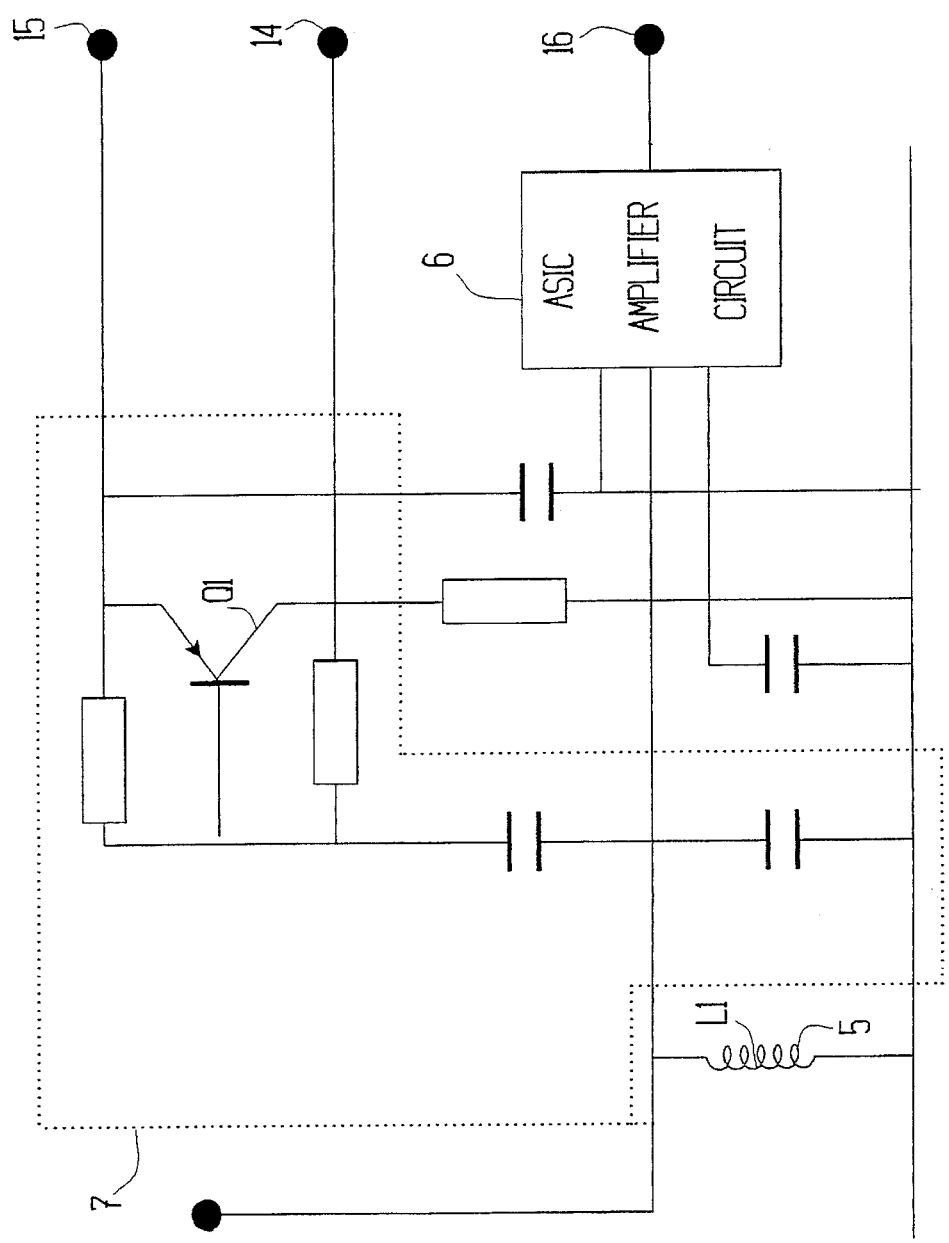
FIG. 2 illustrates a telemetric wireless switch according to the invention.

FIG. 2 shows the detection and amplification stage of the receiver in greater detail, the wireless switch circuit 7 according to the invention being connected to it. An ASIC amplifier circuit 6 comprises the required amplifier stages of the receiver, and its output 16 is directly connectable to the microprocessor controlling the receiver. However, the most essential aspect in view of the invention is the operation of the circuit 7, which may also be integrated in the ASIC circuit 6. In principle, the circuit 7 comprises a transistor Q1 detecting where the intensity of the signal of the receiver coil L1 exceeds a predetermined threshold value. The base of the transistor Q1 is connected to the inductance L1 of the receiver so that when the signal generated by the inductance is of an intensity to actuate a desired function of the pulse meter, the semi-conductor switch is switched on and generates a pulse to a terminal 14 for actuating the pulse measuring function of the pulse meter, for instance. The operating voltage (VCC) of the circuit is supplied from a terminal 15. To be sufficient to start the pulse meter, the signal intensity should be substantially higher (minimum level being of the order of 100 mV, for instance) than the signal intensity required for the actual measurement (such as 10–20 µV). This is achieved by bringing the transmitter close enough to the receiver or in contact with it. In this way the difference between the signals will be several orders of magnitude, which is important for the operability and reliability of the device.

When the pulse measuring function is on, it can be switched off or changed into e.g. the clock function correspondingly by bringing the receiver close enough to the transmitter so that a signal exceeding the predetermined threshold value is obtained in the inductance of the receiver. Additional functions to be actuated by the switch according to the invention during the pulse measuring include display of time for a few seconds, starting of a stopwatch function, etc. This double operation is possible as the switch 7 and the actual receiver circuit 6 have separate couplings 14 and 16 to the processor (not shown) controlling the operation of the receiver, and so the signal intensities below and above the threshold value can be recognized separately during measuring as well.

The device can also be advantageously switched off by the processor after a predetermined time-out period (e.g. 10–15 min) from the last detected pulse signal or the last pressing of a button. In addition, the loudspeaker 11 included in the receiver (FIG. 1) may give an acoustic signal whenever the pulse measuring function is switched on/off or a desired additional function is actuated. This function is easy to program into the receiver if the receiver already comprises a loudspeaker. This has the advantage that the user need not look at the display to ensure that the pulse meter or a desired additional function has been actuated.

It is obvious to one skilled in the art that the different embodiments of the invention are not restricted to the above examples, but they can be varied freely within the scope of the attached claims.

I claim:

1. A wireless switch for a telemetric receiver in a pulse meter, wherein the receiver receives a telemetric pulse measuring signal from a transmitter by means of an inductive coupling between the transmitter and the receiver, the wireless switch, comprising:

means for detecting the intensity of the telemetric pulse measuring signal inductively received in the telemetric receiver and for causing a pulse measuring function of the pulse meter to be activated in the receiver at times when the signal intensity exceeds a predetermined threshold value, the activated pulse measuring function being terminated by causing a second telemetric pulse measuring signal having an intensity exceeding said threshold value to occur in the inductance of the receiver at times when the pulse measurement function is active wherein the means for detecting the intensity of the telemetric pulse measuring signal includes the same inductance used by the receiver for the inductive coupling of the transmitter.

2. A wireless switch according to claim 1, wherein the pulse measuring signal intensity having the predetermined threshold value sufficient to activate said function of the pulse meter is substantially greater than the signal intensity required for the inductive coupling to effect actual pulse measurement without said activation.

3. A wireless switch according to claim 2, wherein a signal intensity sufficient to activate said function of the pulse meter is obtained by bringing the receiver closer to the transmitter than when effecting actual pulse measurements without said activation.

4. A wireless switch according to any one of claims 1 to 3, wherein the switch comprises a semiconductor switch having a base connected to the inductance of the receiver so that when the intensity of the pulse measuring signal generated by the inductance exceeds the predetermined threshold, the semiconductor switch is switched on and generates a pulse for actuating the function of the pulse meter.

5. A wireless switch for a telemetric receiver in a pulse meter, wherein the receiver receives a telemetric pulse measuring signal from a transmitter by means of an inductive coupling between the transmitter and the receiver, the wireless switch, comprising:

means for detecting the intensity of the telemetric pulse measuring signal inductively received in the telemetric receiver and for activating at least one function of the pulse meter at times when the signal intensity exceeds a predetermined threshold value, the means for detecting the intensity of the telemetric pulse measuring signal including the same inductance used by the receiver for the inductive coupling of the transmitter, and an operating mode of the receiver being changeable at times when the pulse measuring function is active in response to a subsequent signal exceeding said threshold value occurring in the inductance of the receiver.

6. A wireless switch according to claim 5 wherein the pulse measuring signal intensity having the predetermined threshold value sufficient to activate said at least one function of the pulse meter is substantially greater than the signal intensity required for the inductive coupling to effect actual pulse measurement without said activation.

7. A wireless switch according to claim 6 wherein a signal intensity sufficient to activate said at least one function of the pulse meter is obtained by bringing the receiver closer to the transmitter than when effecting actual pulse measurements without said activation.

8. A wireless switch for a telemetric receiver in a pulse meter, wherein the receiver receives a telemetric pulse measuring signal from a transmitter by means of an inductive coupling between the transmitter and the receiver, the wireless switch, comprising:

means for detecting the intensity of the telemetric pulse measuring signal inductively received in the telemetric receiver and for activating at least one function of the pulse meter including the pulse measuring function at times when the signal intensity exceeds a predetermined threshold value, the means for detecting the intensity of the telemetric pulse measuring signal including the same inductance used by the receiver for the inductive coupling of the transmitter;

and a loudspeaker included in the receiver to give an acoustic signal at times when the pulse measuring function is switched on or off, or at times when an operating mode of the receiver changes.

9. A wireless switch according to claim 8 wherein the pulse measuring signal intensity having the predetermined threshold value sufficient to activate said at least one function of the pulse meter being substantially greater than the signal intensity required for the inductive coupling to effect actual pulse measurement without said activation.

10. A wireless switch according to claim 9 wherein a signal intensity sufficient to activate said function of the pulse meter is obtained by bringing the receiver closer to the transmitter than when effecting actual pulse measurements without said activation.

* * * * *